(12) United States Patent
Herzlinger

(10) Patent No.: US 7,818,189 B2
(45) Date of Patent: Oct. 19, 2010

(54) ONE-STOP SHOPPING SYSTEM AND METHOD

(75) Inventor: Regina E. Herzlinger, Belmont, MA (US)

(73) Assignee: Regina Herzlinger, Belmont, MA (US)

( * ) Notice: Subject to any disclaimer, the term of this patent is extended or adjusted under 35 U.S.C. 154(b) by 305 days.

(21) Appl. No.: 11/877,601

(22) Filed: Oct. 23, 2007

(65) Prior Publication Data

US 2008/0126421 A1  May 29, 2008

Related U.S. Application Data

(60) Provisional application No. 60/854,847, filed on Oct. 27, 2006.

(51) Int. Cl.
*G06Q 40/00* (2006.01)
*G06F 17/30* (2006.01)

(52) U.S. Cl. .......................... 705/4; 707/806

(58) Field of Classification Search ............. 705/1, 705/2, 4; 707/3, 100, 770, 806
See application file for complete search history.

(56) References Cited

U.S. PATENT DOCUMENTS 6,636,585 B2  10/2003  Salzberg et al.
2002/0007286 A1*  1/2002  Okamoto ................. 705/2
2004/0085345 A1  5/2004  Galou et al.
2004/0260577 A1  12/2004  Dahlin et al.
2005/0075931 A1*  4/2005  Pearson ................. 705/14
2006/0041450 A1*  2/2006  Dugan .................. 705/2
2006/0149595 A1*  7/2006  Williams et al. ........... 705/2
2007/0083449 A1*  4/2007  Roberts ................. 705/35
2007/0276703 A1*  11/2007  Mason et al. ............. 705/4
2008/0059251 A1*  3/2008  Biorge .................. 705/4
2009/0254402 A1*  10/2009  Beall ................... 705/8

OTHER PUBLICATIONS

International Search Report for International Patent Application No. PCT/US07/82279, May 7, 2008, 2 pages.

\* cited by examiner

*Primary Examiner*—Cheryl Lewis
(74) *Attorney, Agent, or Firm*—Wilmer Cutler Pickering Hale and Dorr LLP

(57) ABSTRACT

A system and method are disclosed for one-stop shopping for health-care services and related needs. The one-stop shopping system and method provide objective information for the system enrollee to assess and decide on health-care insurance and services. The system and method provide this objective information in a way that is easily accessible by system enrollees in an economical and rapid manner.

18 Claims, 2 Drawing Sheets

ONE-STOP SHOPPING SYSTEM AND METHOD

RELATED APPLICATIONS

The present application claims priority to provisional application Ser. No. 60/854,847, titled One Stop Shopping System, filed Oct. 27, 2006.

FIELD OF THE INVENTION

The present invention relates to systems and methods that are used for providing information with regard to health-care, health-care related services, and health insurance.

BACKGROUND OF THE INVENTION

Consumer Driven Health Care (CDHC) policies have been developed for employees of companies, individuals and groups (collectively "Insureds") for obtaining health-care services in a manner that the underwriting insurers can be assured that these Insureds are obtaining economically reasonable health-care services and not needlessly overpaying for them. Typically, these policies contain a high-deductible. Thus, they require the Insureds to obtain quotes from more than one service provider to obtain the best value. However, many Insureds have found it very difficult to find the needed health-care information.

To meet the needs of the growing number of Insureds that are covered by defined contribution approaches or CDHC policies, insurers have increased the amount of information that is available on web-based tools. These web-based tools provide the Insureds with quickly accessible information that they can use for obtaining and evaluating health insurance policies, health-care providers, and related health-care services. The information that these insurers provide may be slanted beneficially on behalf of the insurers because they can control the amount and content of the information that is posted on these web-based tools. Accordingly, the Insureds have no assurance that the information is objective and consider their interests.

There are a number of reasons why the Insureds should not feel any comfort in the information that is provided by the insurers. One is that the insurers are unlikely to provide information that conflicts with their business interests, namely to maximize the return to their investors and minimize the amount paid out in claims. Therefore, information made available to the Insureds from insurer controlled web-based tools should not be felt to be particularly reliable from the Insureds' of view. As such, the Insureds must take actions to verify the information that is insurer provided. One such course of action when the information is mistrusted is to obtain a second opinion. Another action is to do extensive research when an enrollee feels that the insurer-provided information is simply not enough for the Insured to make a decision based on such information.

Insureds would prefer to have needed information available from a number of independent sources so that they can make judicious comparisons of health insurance policies, health-care providers, and related health-care services, and the costs and/or prices associated with each of them. In the past, the sources of such information were not in any type of central depository where it could be readily obtained and compared. All that was available to the Insureds were pieces of information at disparate locations, which had to be somehow found and amassed to assist them to make health-care decisions. Therefore, unless the Insureds had a great deal of time and resources, integrated, relevant, and timely information was essentially unavailable to help them make health-care decisions. Noting this, it is highly desirable for there to be a single system that will make needed health-care information readily available from neutral third party sources to assist the Insureds in making health-care decisions in an economically and judicious manner.

SUMMARY OF THE INVENTION

The present invention is a system and method for providing one-stop shopping, among other things, for health-care services. It is understood that the preferred embodiment of the present invention is for providing one-stop shopping for health-care services but the present invention may be used for one-stop shopping of other services and still be within the scope of the present invention.

With regard to the one-stop shopping system of the present invention, health-care information is provided from objective third party sources so that system enrollees may be readily provided with the necessary information to make health-care decisions. This information may be for both the health-care and non-health-care needs of the system enrollee. For example, the non-health-care information may be directed to legal assistance information associated with the administration of health-care related matters.

The system and method of the present invention may be embodied in a computer-based system through which an enrollee would be able to obtain objective information on a number of health-care and non-health-care matters. The computer-based system includes an Application Service Provider (ASP). This information may include, but not be limited to, the following topics:

1. Legal assistance
2. Tracking personal health-care
3. Choosing a health insurance policy
4. Managing a health savings account
5. Maximizing health
6. The siding and selecting medical treatments
7. Selecting doctors, hospitals, and other medical care providers
8. Second opinions
9. Rating medical care providers and insurers
10. Obtaining prices of medical care providers and pharmaceuticals
11. Interacting with insurers The preferred components of the system and method of the present invention include enrollee operated units, the ASP for controlling the flow of information for the one-stop shopping system, and remote information sources for providing objective third-party information to the system enrollees. The system and method of the present invention may be implemented using a wireless or wired communications network.

The system enrollees, through the enrollee operated units, are able to access the ASP for inputting and receiving information. The ASP may include a control unit, a system unit that will be used by the system operator, and a number of system databases that are used for storing information that is input by the enrollee or retrieved based on enrollee requests.

The ASP may be connected to streaming or other data feeds to provide current information in response to enrollee requests. The ASP may also be connected to an external database that contains the health-care records of the enrollee. Further, the ASP may be connected to an external database that includes economic data relating to an enrollee. Even further, the ASP may be connected to an external database that includes information related to an enrollee's health savings account.

The system and method of the present invention, as just described, will enable the enrollee to readily obtain objective information in regard to health insurance policies, health-care providers, health-care services and health-care related information so that the system enrollee can make reasoned decisions about his/her health-care needs through one system.

An object of the present invention is to provided system and method that will readily provide easily accessible information that a system enrollee can use for making economical and judicious health-care decisions.

Another object of the present invention to provide a system and method that will allow system enrollees to have a single location through which they may timely obtain in depth information for use in making economical and judicious health-care decisions.

These and other objects of the invention will be explained in greater detail in the remainder specification with references to the drawings.

DETAILED DESCRIPTION OF THE INVENTION

The present invention is a system and method for one-stop shopping for health-care services and related needs. The one-stop shopping system and method of the present invention provide objective information to a system enrollee. The present invention provides this objective information in a way that is easily accessible by system enrollees in an economically and rapid manner.

Figure 1:
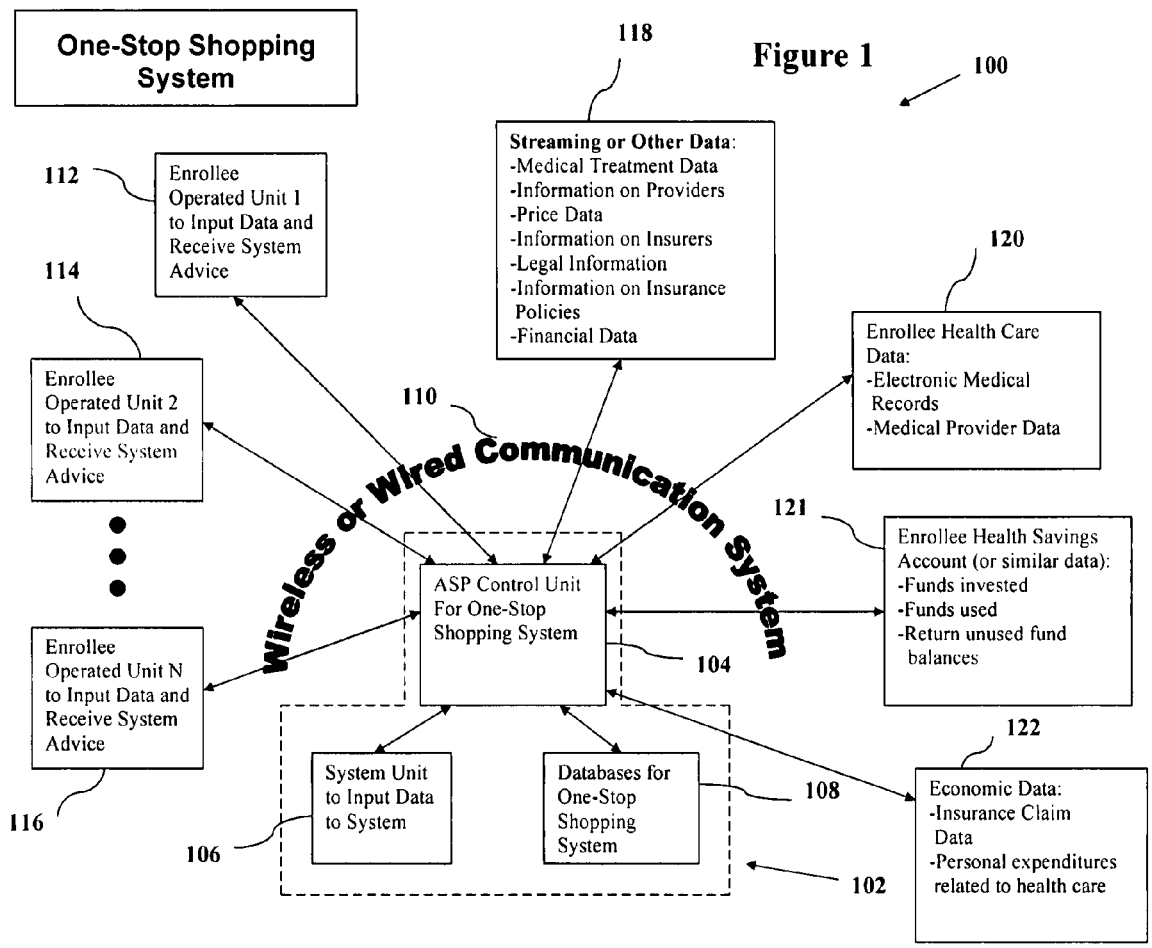
FIG. 1 shows a schematic block drawing of the preferred embodiment system of the present invention.

FIG. 1, generally at 100, shows a schematic block diagram of the preferred embodiment of the system and method of the present invention. The main element of the one-stop shopping system of the present invention is shown generally at 102. At 102 is an ASP that includes control unit 104 that controls the operation of the one-stop shopping system. In communication with control unit 104 is system unit 106 that is also part of the ASP. System unit 106 is operated by the system operator. System unit 106 is used for inputting data to the system and system databases. System unit 106 also may be used for controlling the operation of control unit 104.

System databases 108 connect to control unit 104 of ASP 102. System databases 108 will consist of a plurality of databases that are used for storing health-care information that an enrollee may request. Typically, the information that is stored in system databases 108 includes information that is retrieved based on enrollee requests. When changes to this information or additional information is to be stored in system databases 108, these databases will be appropriately updated. An example of information that may be stored in one of the system databases includes information about health-care providers in the enrollee's area.

Communications to and from ASP 102 may be through a wired or wireless network, as shown at 110. The wired network could be a local area network (LAN), municipal area network (MAN), wide area network (WAN), or an intranet. The wireless network could be the Internet or the World Wide Web. Each of these communications networks, both wired and wireless, are within the scope of the present invention.

Enrollee operated units for the one-stop shopping system of the present invention are shown at 112, 114, and 116. These units include personal computers, personal digital assistants, cellular telephones, or other similar devices capable of communicating with the ASP electronically or otherwise. The three enrollee operated units are meant to the representative of any number of enrollee operated units that access ASP 102. Each enrollee operated unit may be used, for example, to input data that will be used to retrieve information that is stored in system databases or external databases. The enrollee operated units also may be used for inputting data for storage either in system databases 108 or external databases. The information that is retrieved by the enrollee at the enrollee operated units may be on a variety of topics with respect to the enrollee's health insurance policy, health-care providers, and health-care services needs.

Again referring to FIG. 1, there is a large amount of data that the enrollee may retrieve and store in the system databases shown at 108. The information at remote locations that may be accessed by the enrollee through ASP 102 includes streaming and other data at 118, enrollee health-care data at 120, enrollee health savings account data at 121, and economic data at 122. Although, there are only four types of data sources shown, it is understood that there may be more or less than four types of data sources and still be within the scope of the present invention.

Referring to data source 118, titled "Streaming or Other Data," the information provided from this data source includes information that typically changes rapidly. The data that is available from data source 118 may include the latest medical treatment data for diseases and other medical conditions, information about health-care service providers, current pricing data for specific health-care services, information on insurers, for example, relating to coverage, legal information as it applies to health-care providers, insurers, and others, information on insurance policies, e.g., comparisons of current information on policies from various insurers or different policies by one insurer, and financial data with respect to the insurance industry.

The "Streaming or Other Data" that has just been discussed is only an example of the streaming or other data that may be available to the enrollee through the ASP; it being understood that more or less information than is listed may be available through this information data source and still be within the scope of the present invention.

Referring to data source 120, titled "Enrollee Health Care Data," the information provided through this data source may be medical information with regard to the enrollee that may be stored at a remote location, e.g., an electronic medical record or computerized medical record. Typically, the information from this data source could only be retrieved if authorized by the enrollee. However, a physician or hospital would have access to the electronic medical record for inputting data to it without requesting to do so from the enrollee. Moreover, it could be the case that the physician and/or hospital would have a right to retrieve information from electronic record without requesting to do so from the enrollee. Information that is stored in an electronic medical record may include health-care information about a specific enrollee or information about the enrollee's medical provider.

The "Enrollee Health Care Data" that has just been discussed is only an example of the data that may be available to the enrollee through the ASP relating to the enrollee health; it being understood that more or less information may be available through this information data source and still be within the scope of the present invention.

Referring to data source 121 titled "Enrollee Health Savings Account Data," the information provided through this data source may include information related to funds invested, funds used, and the return of unused fund balances with regard to enrollee health savings accounts. The information that is provided from this data source may only be available if authorized by the enrollee. However, the institution that holds enrollee health savings account would have the right to access the account for inputting data to it without requesting to do so from the enrollee.

The "Enrollee Health Savings Account Data" that has just been discussed is only an example of the health savings account data that may be available to the enrollee through the ASP; it being understood that more or less information may be available through this information data source and still be within the scope of the present invention.

Referring to data source 122 titled, "Economic Data," the information provided through this data source may include insurance data relating to the enrollee or specific insurance data with respect to the enrollee's insurer, or data relating personal expenditures by the enrollee with regard to his/her health care. The insurance data may include insurance claim data with respect to the enrollee. The personal expenditure data may, for example, refer to amounts that the enrollee actually paid for treatment. The information that is provided from this data source may only be available if authorized by the enrollee. However, it is understood, for example, that some economic data sources relating to enrollee insurance and insurance policies may have their access controlled by the enrollee and/or the insurance policy underwriter and still be within the scope of the present invention.

The "Economic Data" that has just been discussed is only an example of the economic data that may be available to the enrollee through the ASP; it being understood that more or less information may be available through this information data source and still be within the scope of the present invention.

As discussed in the Summary of the Invention, information that may be available to the enrollee through the one-stop shopping system of the present invention may include the following:
1. Legal assistance
2. Tracking personal health-care
3. Choosing a health insurance policy
4. Managing a health savings account
5. Maximizing health
6. Selecting medical treatments
7. Selecting doctors, hospitals, and other medical care providers
8. Second opinions
9. Rating medical care providers and insurers
10. Obtaining prices of medical care providers and pharmaceuticals
11. Interacting with insurers In greater detail, the legal assistance information that may be provided would include information on possible class actions or other types of legal activities taking place that may impact the enrollee.

Tracking of enrollee's personal health-care information may be information accessed in the enrollee's electronic medical record. In accessing this information, enrollee can ensure that such information contained in the electronic medical record is accurate at all times.

Information that may be available for the enrollee that relates to selecting a health insurance policy may include information from a data source such as the eBenefits web site. This information may include comparative information on health insurance policies sufficient for the enrollee to make an informed decision on the policy to select.

An enrollee's management of his/her health savings account may include information about the actual amounts in a health savings account. More specifically, through the system of the present invention, an enrollee can view his/her account, for example, at Fidelity Investments to know the status of the account including that the account is being properly charged for health-care services.

The enrollee also can use the one-stop shopping system of the present invention to maximize his/her health. This may be carried out by using the system to obtain information on possible health risks and track health information, for example, that is associated with a new drug or the susceptibility of certain individuals to adverse affects with regard to certain treatments.

According to the above, an enrollee can be provided sufficient information to assess and select appropriate treatments for specific medical conditions. This could include treatments in the form of therapy for a particular condition. It could also provide locations where appropriate medical treatment can be provided for the enrollee's specific condition.

One of the principal areas of information to be provided to an enrollee by the one-stop shopping system of the present invention is information relating to the selection of high-quality doctors, hospitals, and other health-care providers. This will not only include the names of good doctors, hospitals, and other health-care providers but will provide in-depth information about these entities so that the enrollee can better judge whether a particular health-care provider would be good for him/her.

An enrollee also will be provided information that will permit him/her to obtain as many opinions as he/she may desire with respect to a specific medical condition of that enrollee. This can be very important to the enrollee in situations where he/she feels very uncomfortable with the first opinion that was obtained. Moreover, it will provide an ability to obtain these further opinions without placing the enrollee in the uncomfortable position of needing to seek recommendations for these further opinions from the person who provided the initial opinion.

There are a number of information data sources that provide information relating to ratings of health insurance policies, health-care providers, and health-care services. However, this information is not usually accessible at a single convenient location. The one-stop shopping system of the present invention will provide such rating information to the enrollee. This rating information may not only be helpful to enrollees but also to health-care providers and insurers.

Another principal area of the one-stop shopping system of the present invention is providing enrollees with information directed to prices for health-care services from health-care providers and for pharmaceuticals. The information that may be available would be prices for comparable health-care services in specific areas of medical practice and for pharmaceuticals, such as drugs and their generics. This information may be helpful to the enrollee in obtaining insurance coverage for their particular condition for which insurance coverage is sought including information about available generics.

The one-stop shopping system of the present invention also provides information to the enrollee regarding dealing with specific insurers. For example, it may provide information on what insurers require by way of documentation before reimbursements will be paid. Accordingly, using the present invention, the enrollee can obtain information on various insurers in order to promptly obtain reimbursement for charges. An example is a household where a husband and wife are both employed by two separate companies that provide insurance coverage for them. The two insurance companies may have specific procedures to be followed for obtaining reimbursement by this couple. Additionally, the data source may provide information relating to enrollee satisfaction with different insurers and insurance policies.

Figure 2:
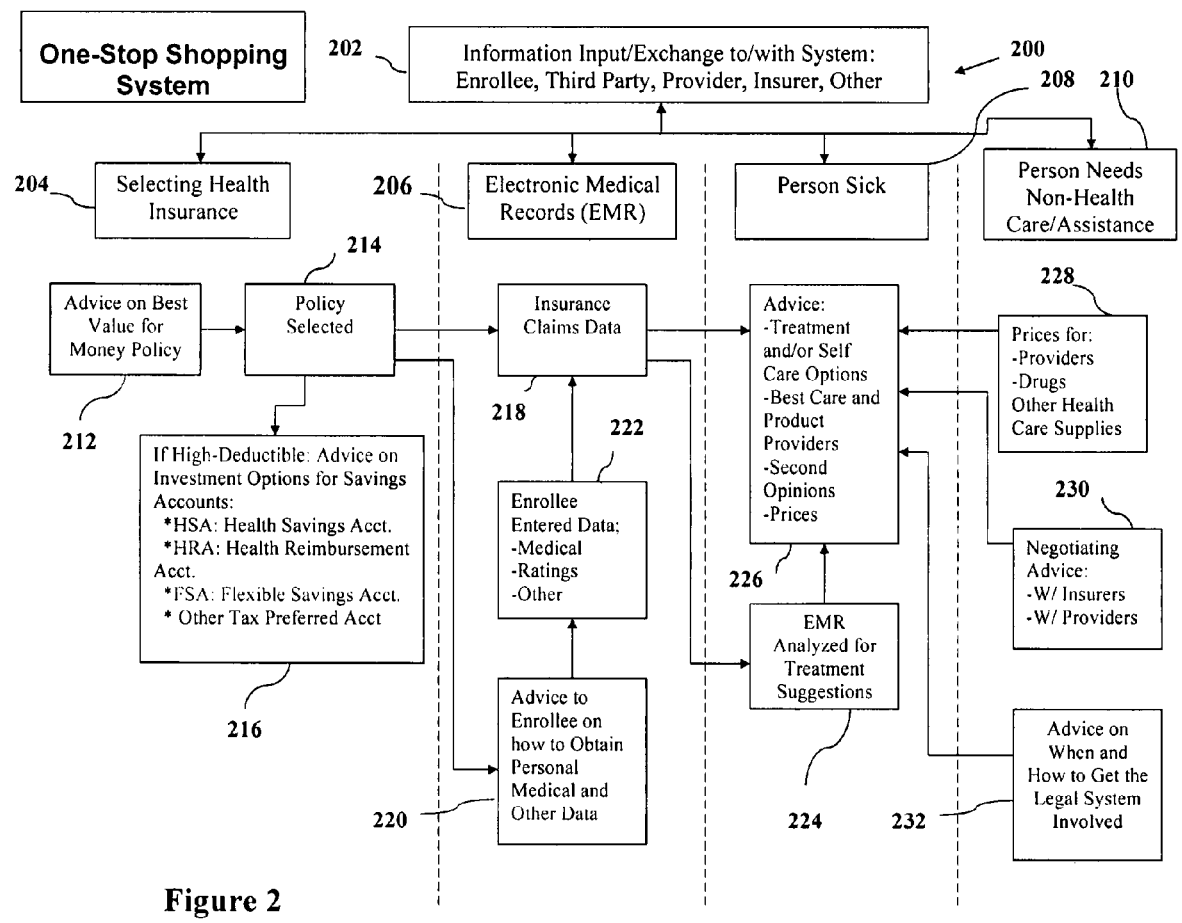
FIG. 2 shows a schematic block drawing of an embodiment of the information exchange with respect to the system and method of the present invention shown in FIG. 1 between the enrollee, third parties, service providers, insurers, and others.

FIG. 2, generally at 200, shows a schematic block diagram of an example of information that may be exchanged using the one-stop shopping system of the present invention. The exchange of information is between enrollee operated units 112, 114, or 116; control unit 104 of ASP 102; the system operator through system unit 106; system databases 108; remote sites such as data source 118 for streaming and other data; data source 120 for enrollee health-care data; data source 121 for enrollee health savings account data; and data source 122 for economic and personal expenditure data.

Referring again to FIG. 2, generally at 202, a view of the information exchange from the standpoint of ASP 102 is shown. Control unit 104 will control the processing information for the one-stop shopping system of the present invention. This information will be distributed among enrollees, insurers, third parties, health-care providers, and others. The dynamic exchange of information is predicated on the requests that are provided by the enrollee through enrollee operated units 112, 114, and 116.

As shown in FIG. 2, there are four general areas for which information is exchanged. These are selecting health insurance 204, medical records information 206, information associated with the enrollee being sick (person sick) at 208, and non-health-care related assistance 210.

Taking first selecting health insurance 204, the enrollee would be provided information at 212 regarding the best policy values for the money that the enrollee is willing to pay from, for example, retrieved from streaming or other data source 118 and stored in system databases 108. The information provided at 212 would be policies from various insurance providers so that the enrollee can make an initial choice. Based on this information, the enrollee selects a policy at 214. In selecting the policy, the enrollee will consider economic issues such as shown at 216. For example, if the deductible were high, the enrollee would be given advice with respect to investment options on savings related to these accounts. Once the policy is selected, the enrollee will then be prepared to retrieve information should there be a need to make a claim against the insurance policy.

Referring to sick person at 208, when an enrollee become sick, the one-stop shopping system of the present invention is used to provide assistance in finding the appropriate treatment for the enrollee and proper reimbursement based on the selected insurance policy. It is understood that there are a number of things that need to take place with respect to potential reimbursement for expenses for the enrollee and other non-medical issues; however, the first item is to find a diagnosis and proper treatment for the enrollee's condition. To arrive at the appropriate treatment, it is necessary to understand what options the enrollee will have the respect to his/her insurance coverage. For example, if the potential costs for treatment for the enrollee would be $3000 for one medical service provider and $2000 for another equally capable service provider and the enrollee's reimbursable ceiling under his/her insurance policy is $2000, then it will be appropriate for the enrollee to select the latter service provider unless that enrollee wishes to pay $1000 out of pocket. Therefore, before a treatment is selected, information about the enrollee's insurance claims data must be considered. The information that is retrieved for this consideration may be from the streaming or other data source 118 that is directed to information from health-care providers and health-care sources. The retrieved information may be stored in system databases 108.

The electronic medical record at 206 is the permanent record of the medical information about the enrollee. As indicated above, access to such electronic medical record information is typically only available when authorized by the enrollee. Information retrieved from an electronic medical record that may be stored in system databases 108 may be used for a number of things. It may be exchanged with an insurance policy underwriter for purposes of making an insurance claim or it may be used in determining the appropriate treatment advice.

Should it become necessary for an enrollee to make an insurance claim, it will be necessary for that enrollee to provide insurance claim data at 218. Advice on the insurance claims data is generated through boxes 220 and 222. At 220, the enrollee is provided advice on how to obtain personal medical data, for example, from the electronic medical record. At 222, the enrollee through his/her enrollee operated unit enters the appropriate information that has been received from the advice at 220. This information forms of the insurance claims data at 218.

After the insurance claims data is determined at 218 based on information from the enrollee's electronic medical record, the electronic medical record is analyzed at 224 to determine the possible treatment options that are available for the enrollee's particular condition. This analysis may be carried out based on information retrieved from streaming or other data source 118. Once this analysis is complete, then treatment advice is provided at 226. Typically, this treatment will be within the reimbursable parameters of the insurance claims data that is provided at 218. This advice may include treatment information and/or self-care options, the best care products and health-care service providers, second and third opinions if needed, and the price of the particular recommended treatments.

The advice that is given at 226 also will include non-health-care information at 210. For example, information provided at 228 may be information about prices for particular health-care providers, drugs, and other health-care supplies, e.g., wheelchair rental.

The advice at 226 may be accompanied by negotiating advice at 230. This information may be how to negotiate the best prices from certain health-care providers or negotiating extensions of coverage with insurers.

The advice at 226 also may be supplemented with the advice at 232. This advice may include when and how the enrollee should involve the legal system with regard to obtaining his/her rightful insurance coverage or actions against third parties with respect to the care given or the causes of the harm to the enrollee.

The information exchange that is shown in FIG. 2 is directed to a preferred embodiment of information exchange that may take place with respect to the one-stop shopping system of the present invention. As would be understood by a person of ordinary skill in the art, although the present invention is directed to one-stop shopping to the obtain health-care information and advice, the one-stop shopping system of the present invention would apply to other areas that are not related to health-care and still be within the scope of the present invention.

The terms and expressions that are used herein are meant for description not limitation, it being recognized that there may be minor changes or modifications that must take place and be within the scope of the present invention.

The invention claimed is:

1. A single-integrated system for a system enrollee to obtain request-based information for taking remedial-based action, comprising:
    at least one enrollee operated unit for an enrollee to input information to the single-integrated system and requests for information relating to health-care for which remedial action is desired, and for receiving retrieved information with regard to health-care for which remedial action is desired;
    a control means for processing and controlling a flow of enrollee requests and retrieved information, with such retrieved information being related at least to health-care for which remedial action is desired;
    a first set of data sources that contain rapidly changing content including at least medical treatment information, with the first set of data sources being capable of providing retrieved medical treatment information in response to enrollee requests that is a current, up to date version of such medical treatment information at a time an enrollee request accesses at least one of the first set of data sources;
    a second set of data sources that contain enrollee specific information, with such second set of data sources having accessibility controlled by the enrollee for purposes of inputting information to and retrieving enrollee specific information from such second set of data sources;
    a third set of data sources that contain enrollee and at least one third party information including at least enrollee insurance information, with the enrollee and at least one third party controlling accessibility for purposes of inputting information to and retrieving information from such third set of data sources, and with the retrieved enrollee insurance information being used to determine a best health-care treatment for the enrollee according to insurance coverage limits;
    a fourth set of data sources that contain non-healthcare information including at least legal information, with the fourth set of data sources providing retrieved non-healthcare information in response to enrollee requests for such non-healthcare information; and
    a communications network for connecting the control means to the at least one enrollee operated unit, the first set of data sources, the second set of data sources, the third set of data sources, and the fourth set of data sources.

2. The system as recited in claim 1, wherein the control mean includes an Application Service Provider (ASP).

3. The system as recited in claim 2, wherein the communications network includes a wireless network.

4. The system as recited in claim 3, wherein the wireless network includes the Internet.

5. The system as recited in claim 3, wherein the wireless network includes a World Wide Web.

6. The system as recited in claim 2, wherein the communications network includes a wired network.

7. The system as recited in claim 2, wherein the ASP further includes
    a control unit for processing and controlling the flow of enrollee requests and retrieved information, with such retrieved information being related at least to health-care for which remedial action is desired,
    a system unit for controlling operation of the ASP, and
    at least one system database for storing information input thereto by the enrollee and retrieved information from the first set of data sources, second set of data sources, third set of data sources, or fourth set of data sources.

8. The system as recited in claim 2, wherein information from the first set of data sources includes streaming data information.

9. The system as recited in claim 2, wherein information from the second set of data sources includes electronic medical record information.

10. The system as recited in claim 2, or any information from the second set of data sources includes enrollee health savings account information.

11. A method for an enrollee to obtain request-based information for taking remedial-based action, comprising the steps of:
    (a) the enrollee determining health-care for which remedial action is desired and generating at least one request for transmission to a single-integrated system for obtaining requested information;
    (b) the single-integrated system processing the at least one request and controlling the transmission of the request, if needed, to a first set of data sources containing rapidly changing content including at least medical treatment information, with the first set of data sources being capable of providing retrieved medical treatment information in response to the enrollee request that is a current, up to date version of medical treatment information at a time the enrollee request accesses at least one of the first set of data sources, with the single-integrated system retrieving information from at least one of the first data sources based on the at least one enrollee request and storing the retrieved information in a storage means;
    (c) the single-integrated system processing the at least one request and controlling the transmission of the request, if needed, to a second set of data sources that contain enrollee specific information, with such second set of data sources having accessibility controlled by the enrollee for purposes of inputting information to and retrieving enrollee specific information from such second set of data sources, with the single-integrated system retrieving information from at least one of the second data sources based on the at least one enrollee request and storing the retrieved information in the storage means;
    (d) the single-integrated system processing the at least one request and controlling the transmission of the request, if needed, to a third set of data sources that contain enrollee and at least one third-party information including at least enrollee insurance information, with the enrollee and at least one third party controlling accessibility for purposes of inputting information and retrieving information from such third set of data sources, with the retrieved enrollee insurance information being used to determine a best health-care treatment for the enrollee according to insurance coverage limits, and with the single-integrated system retrieving information from at least one of the third data sources based on the at least one enrollee request and storing the retrieved information in the storage means;
    (e) the single-integrated system processing the at least one request and controlling the transmission of the request, if needed, to a fourth set of data sources that contain non-healthcare information including at least legal information, with the single-integrated system retrieving information from at least one of the fourth data sources based on at least one enrollee request and storing the retrieved information in the storage means; and
    (f) the enrollee accessing the storage means for retrieving retrieved information from the first set of data sources, second set of data sources, third set of data sources, and/or fourth set of data sources, and taking a remedial action based on the retrieved information.

12. The method as recited in claim 11, wherein the single-integrated system includes a control means and the control means includes an Application Service Provider (ASP).

13. The method as recited in claim 12, wherein communications among the enrollee and the first set of data sources, second set of data sources, third set of data sources, and/or fourth set of data sources through the ASP includes wireless communications.

14. The method as recited in claim 12, wherein communications among the enrollee and the first set of data sources, second set of data sources, third set of data sources, and/or fourth set of data sources through the ASP includes wired communications.

15. The method as recited in claim 12, wherein storing in storing means includes storing in system databases.

16. The method as recited in claim 12, wherein retrieving information from the first set of data sources includes retrieving streaming data information.

17. The method as recited in claim 12, wherein retrieving information from the second set of data sources includes retrieving electronic medical record information.

18. The method as recited in claim 12, wherein retrieving information from the second set of data sources includes retrieving enrollee health savings account information.

* * * * *